(12) United States Patent
Franke

(10) Patent No.: US 7,556,705 B2
(45) Date of Patent: Jul. 7, 2009

(54) PROCESS FOR SEPARATING A PRODUCT WEB INTO DISCRETE PRODUCTS

(75) Inventor: Mark S. Franke, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 580 days.

(21) Appl. No.: 11/215,875

(22) Filed: Aug. 30, 2005

(65) Prior Publication Data

US 2007/0044608 A1    Mar. 1, 2007

(51) Int. Cl.
A61F 13/15     (2006.01)
B32B 38/04     (2006.01)

(52) U.S. Cl. .................. 156/204; 156/226; 156/252
(58) Field of Classification Search .................. None
See application file for complete search history.

(56) References Cited

U.S. PATENT DOCUMENTS

| | | | | |
|---|---|---|---|---|
| 3,820,447 A | * | 6/1974 | Gendron et al. | 493/188 |
| 3,899,381 A | * | 8/1975 | O'Brien et al. | 156/204 |
| 4,148,430 A | * | 4/1979 | Drake | 229/69 |
| 4,663,220 A | | 5/1987 | Wisneski et al. | |
| 4,704,116 A | | 11/1987 | Enloe | |
| 5,046,272 A | | 9/1991 | Vogt et al. | |
| 5,226,992 A | | 7/1993 | Morman | |
| 5,565,059 A | * | 10/1996 | Edwards et al. | 156/517 |
| 6,192,521 B1 | | 2/2001 | Alberts et al. | |
| 6,276,054 B1 | * | 8/2001 | Cartmell et al. | 29/825 |
| 6,585,840 B2 | | 7/2003 | Rabe et al. | |
| 7,192,500 B2 | * | 3/2007 | Allen | 156/204 |
| 7,288,162 B2 | * | 10/2007 | Allen | 156/204 |
| 2002/0148557 A1 | * | 10/2002 | Heller et al. | 156/252 |
| 2004/0102746 A1 | | 5/2004 | Mortell et al. | |
| 2005/0145150 A1 | | 7/2005 | Mortell et al. | |
| 2005/0241747 A1 | | 11/2005 | Allen | |
| 2005/0241748 A1 | | 11/2005 | Allen | |
| 2006/0266467 A1 | * | 11/2006 | Mlinar | 156/252 |

FOREIGN PATENT DOCUMENTS

| | | |
|---|---|---|
| EP | 0 217 032 B1 | 2/1992 |
| EP | 1 108 371 A1 | 6/2001 |
| WO | WO 01/87217 A2 | 11/2001 |
| WO | WO 01/87218 A2 | 11/2001 |
| WO | WO 01/87562 A2 | 11/2001 |
| WO | WO 01/87753 A2 | 11/2001 |
| WO | WO 01/88245 A2 | 11/2001 |
| WO | WO 02/00152 A1 | 1/2002 |
| WO | WO 02/49565 A2 | 6/2002 |

* cited by examiner

Primary Examiner—Richard Crispino
Assistant Examiner—Barbara J. Musser
(74) Attorney, Agent, or Firm—John L. Brodersen; Randall W. Fieldhack

(57) ABSTRACT

A process for separating a product web into discrete products is disclosed. The process can include transporting the product web in a machine direction, creating a line of weakness in the product web, and separating the product web into discrete product elements at the line of weakness.

21 Claims, 7 Drawing Sheets

PROCESS FOR SEPARATING A PRODUCT WEB INTO DISCRETE PRODUCTS

The present invention relates generally to a process for separating a product web into discrete products, and particularly to a process where such products can include an absorbent assembly and are intended to be worn about the lower torso.

Garments intended to be worn about the lower torso, such as boxer shorts or other pant-like garments, have a variety of uses including semi-durable garments, disposable garments, and swimwear. Often it may be advantageous for these garments to include an absorbent body; in such configurations, the garments may have applications as training pants, incontinence products, feminine care products, and the like.

Processes for making garments intended to be worn about the lower torso are known in the art. Nonetheless, the processes that are presently available may often result in garments that are not aesthetically pleasing due to uneven edges or loose trim about the waist opening and/or the leg openings of the garment. This can be particularly true in processes where the garment is provided by multiple webs and includes folding or other manipulation of the webs. Further, such processes can become more complex when producing garments in an automated high-speed converting system.

Accordingly, there remains a need for a process that provides products having even edges that are substantially free of trim and that, in certain instances, include an absorbent assembly. Further, there is a need for a process for making such products that is capable of being used in connection with an automated high-speed converting system.

SUMMARY OF THE INVENTION

In one aspect, the present invention is directed to a process for separating a product web into discrete products, the process defining a machine direction and a cross machine direction. The product web defines: a product web first side edge and a product web second side edge opposite the product web first side edge, a product web first surface and a product web second surface opposite the product web first surface, and a product web interior within the product web first side edge and the product web second side edge. The process includes transporting the product web in the machine direction, the product web including a first web and an opening in the product web interior. In addition, the process includes creating a line of weakness in the product web, the line of weakness extending substantially in the cross machine direction. In addition, the process further includes separating the product web into discrete products at the line of weakness.

In another aspect, the present invention is directed to a process for separating a product web into discrete products, the process defining a machine direction and a cross machine direction. The product web defines: a product web first side edge and a product web second side edge opposite the product web first side edge, a product web first surface and a product web second surface opposite the product web first surface, and a product web interior within the product web first side edge and the product web second side edge. The process includes transporting the product web in the machine direction, the product web including a first web and an opening in the product web interior. In addition, the process includes creating a line of weakness in the product web, the line of weakness extending substantially in the cross machine direction. In addition, the process includes directing a portion of the product web in the cross machine direction to define a product web folded portion. In addition, the process further includes separating the product web into discrete elements at the line of weakness.

In yet another aspect, the present invention is directed to a process for separating a product web into discrete products, the process defining a machine direction and a cross machine direction. The product web defines: a product web first side edge and a product web second side edge opposite the product web first side edge, a product web first surface and a product web second surface opposite the product web first surface, and a product web interior within the product web first side edge and the product web second side edge. The process includes transporting the product web in the machine direction, the product web including a first web, a second web attached to the first web and an opening in the product web interior. In addition, the process includes creating a line of weakness in the product web, the line of weakness extending substantially in the cross machine direction. In addition, the process includes directing a portion of the product web in the cross machine direction to define a product web folded portion. In addition, the process further includes separating the product web into discrete products at the line of weakness.

As a result, the present invention provides a distinctive process that is capable of making a garment via a continuous process where the garment features pleasing, even edges and is capable of being run at elevated process speeds. Moreover, the garment can optionally include edges that are curvilinear and/or linear. Further, the garment can optionally include an absorbent assembly. Thus, the process of the present invention is capable of mass producing aesthetically pleasing garments having even edges that are substantially free of trim.

The above-mentioned and other aspects of the present invention will become more apparent, and the invention itself will be better understood by reference to the drawings and the following description of the drawings.

BRIEF DESCRIPTION OF THE DRAWINGS

Corresponding reference characters indicate corresponding parts throughout the drawings.

Definitions

Figure 1:
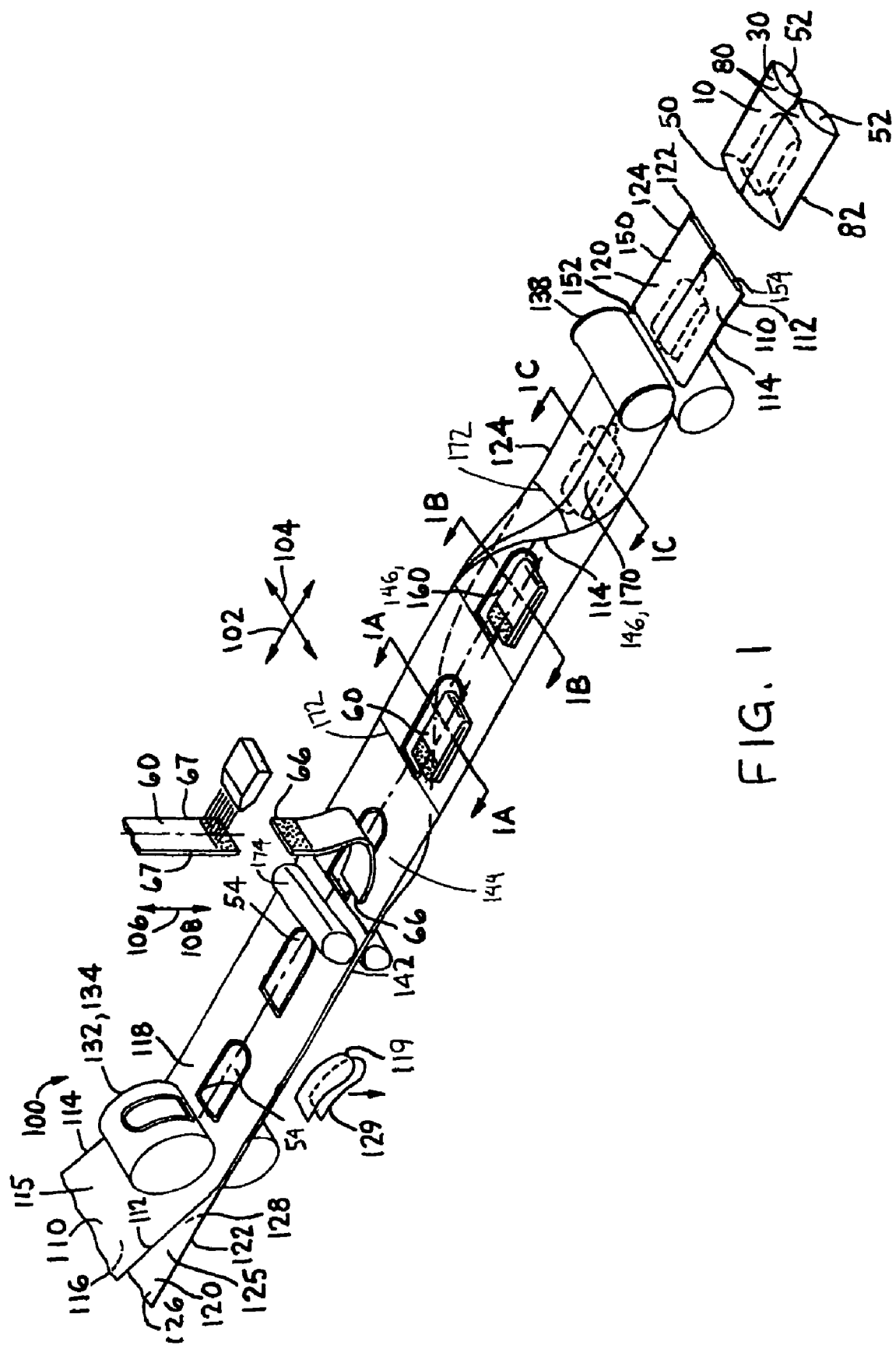
FIG. 1 representatively illustrates a schematic view of one aspect of a process of the present invention.
Figure 1A:
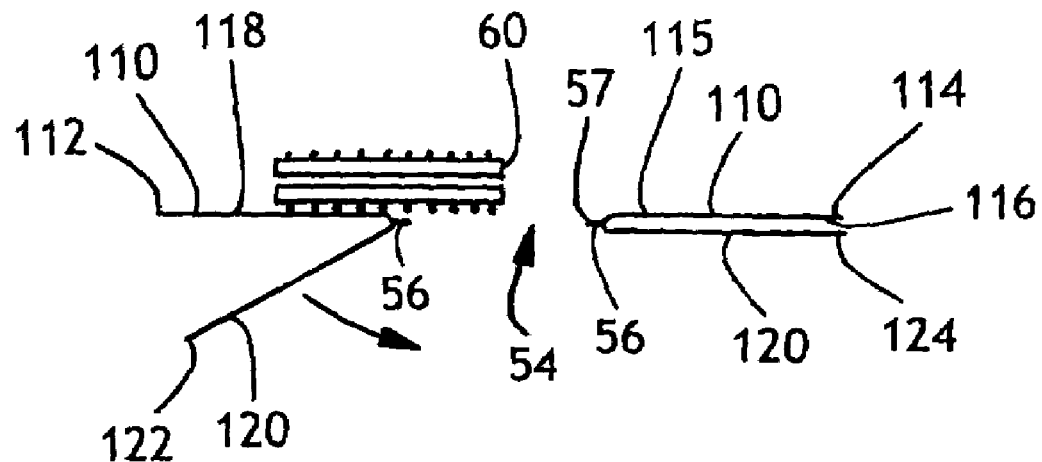
FIGS. 1A-1C representatively illustrate cross section views from FIG. 1 with background portions of the cross sections omitted for clarity.
Figure 1B:
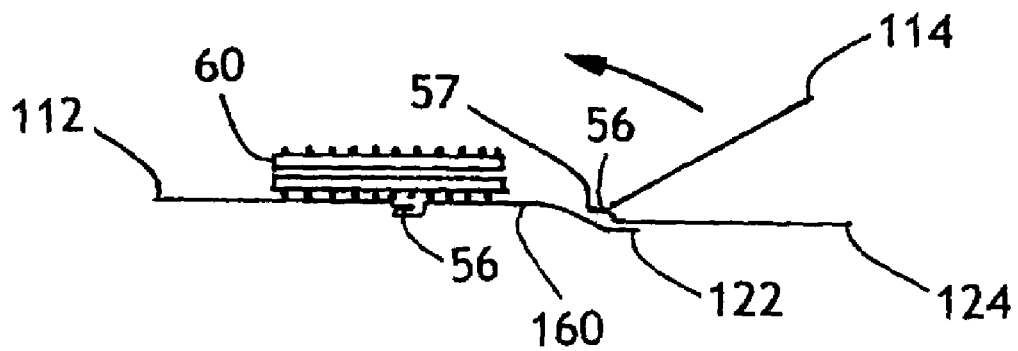
Figure 1C:
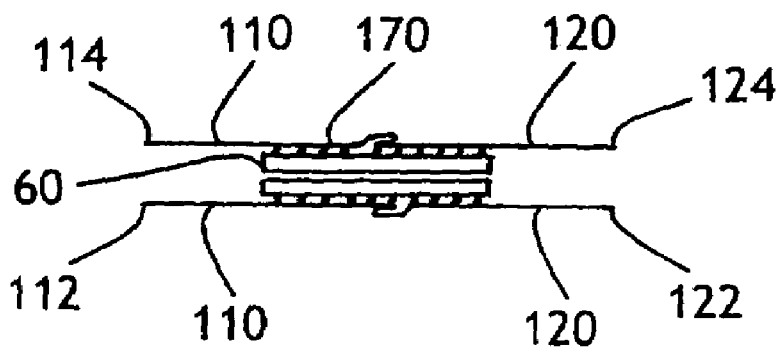

Within the context of this specification, each term or phrase below will include the following meaning or meanings.

"Attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end user.

"Bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements. "Bond" and its derivatives include permanent, releasable, or refastenable bonding.

"Boxer shorts" or "Shorts" refers to pants, trunks, briefs, and the like, and include garments that may be relatively loose fitting or snug at the leg area.

"Connect" and its derivatives refer to the joining, adhering, bonding, attaching, sewing together, or the like, of two elements. Two elements will be considered to be connected together when they are integral with one another or connected directly to one another or indirectly to one another, such as when each is directly connected to intermediate elements. "Connect" and its derivatives include permanent, releasable, or refastenable connection. In addition, the connecting can be completed either during the manufacturing process or by the end user.

"Disposable" refers to articles which are designed to be discarded after a limited use rather than being laundered or otherwise restored for reuse.

The terms "disposed on," "disposed along," or "disposed toward" and variations thereof are intended to mean that one element can be integral with another element, or that one element can be a separate structure bonded to or placed with or placed near another element.

"Downstream" refers to the positioning of one element or event further in the direction of material travel relative to another element or event in a process.

"Elastic," "elasticized," "elasticity," and "elastomeric" mean that property of a material or composite by virtue of which it tends to recover its original size and shape after removal of a force causing a deformation. Suitably, an elastic material or composite can be elongated by at least 25 percent (to 125 percent) of its relaxed length and will recover, upon release of the applied force, at least 10 percent of its elongation. Desirably an elastic material or composite be capable of being elongated by at least 100 percent (to 200 percent), more desirably by at least 300 percent (to 400 percent), of its relaxed length and recover, upon release of an applied force, at least 50 percent of its elongation.

"Fabrics" is used to refer to all woven, knitted and nonwoven fibrous webs.

"Front-to-back crotch seam" refers to a seam extending from the front region to the back region of a pant-style garment, through the crotch region. The seam can join two separate pieces of material, or separate edges of a single piece of material.

"Garment shell" refers to those portions of the articles that can be produced by the process of the present invention that are not part of an absorbent assembly.

"Hanging legs" refers to the characteristic of a garment intended to be worn about the lower torso where the garment includes material that extends below the crotch of the garment and is intended to generally cover at least a portion of the leg of the wearer; the material may be loose fitting about the leg of the wearer, fit snugly about the leg of the wearer and/or may be elastic or non-elastic.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 are designated "wettable" or hydrophilic, while fibers having contact angles greater than 90 are designated "nonwettable" or hydrophobic.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact.

"Machine direction" refers to the direction in which material travels during a production process, as opposed to "cross-machine direction" which refers to the direction that is generally transverse and perpendicular to the machine direction.

"Nonwoven" and "nonwoven web" refer to materials and webs of material that are formed without the aid of a textile weaving or knitting process.

"Open Configuration" refers to the condition that the garment shell web is in before the formation of a waist opening and a pair of leg openings in the article. The garment shell web may be manipulated, have portions directed in the machine direction or the cross machine direction, or may be separated into individual garment chassis and still be in an open configuration, provided that the formation of the waist opening and the leg openings has not yet been completed.

"Overlap" refers to the condition where one element is positioned to be at least partially covering another element either directly or indirectly. It should be noted that one element may be beneath the other element and still be overlapping the other element.

"Pants" includes full length and short pants.

"Stretchable" means that a material can be stretched, without breaking, by at least 25% (to 125% of its initial (unstretched) length) in at least one direction, suitably by at least 100% (to 200% of its initial length), desirably by at least 150% (to at least 250% of its initial length).

"Upstream" refers to the positioning of an element or event further in the direction opposite to the direction of material travel relative to another element or event in a process.

These terms may be defined with additional language in the remaining portions of the specification.

DETAILED DESCRIPTION

Figure 2:
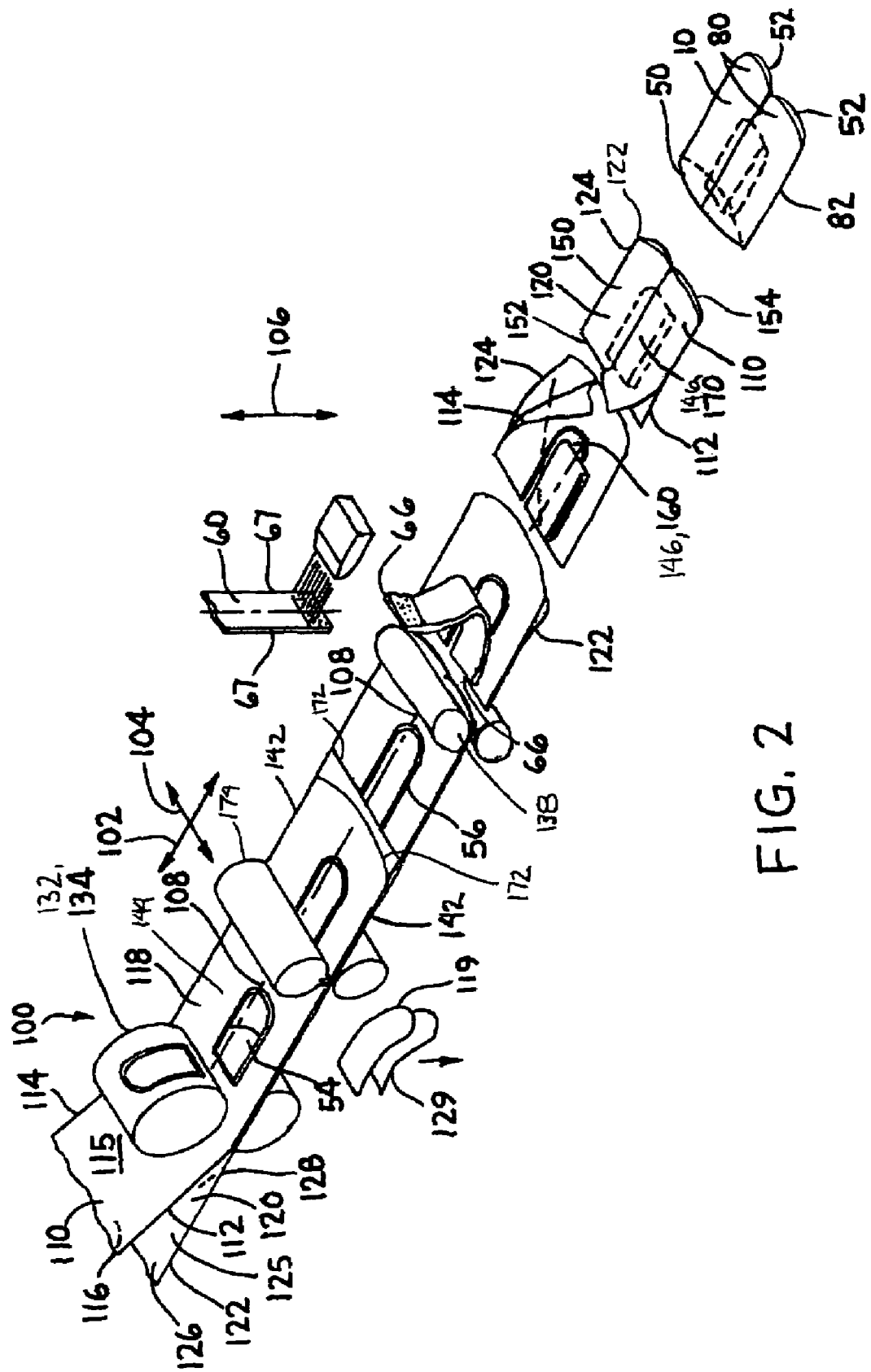
FIG. 2 representatively illustrates a schematic view of another aspect of the process of the present invention similar to FIG. 1.
Figure 3:
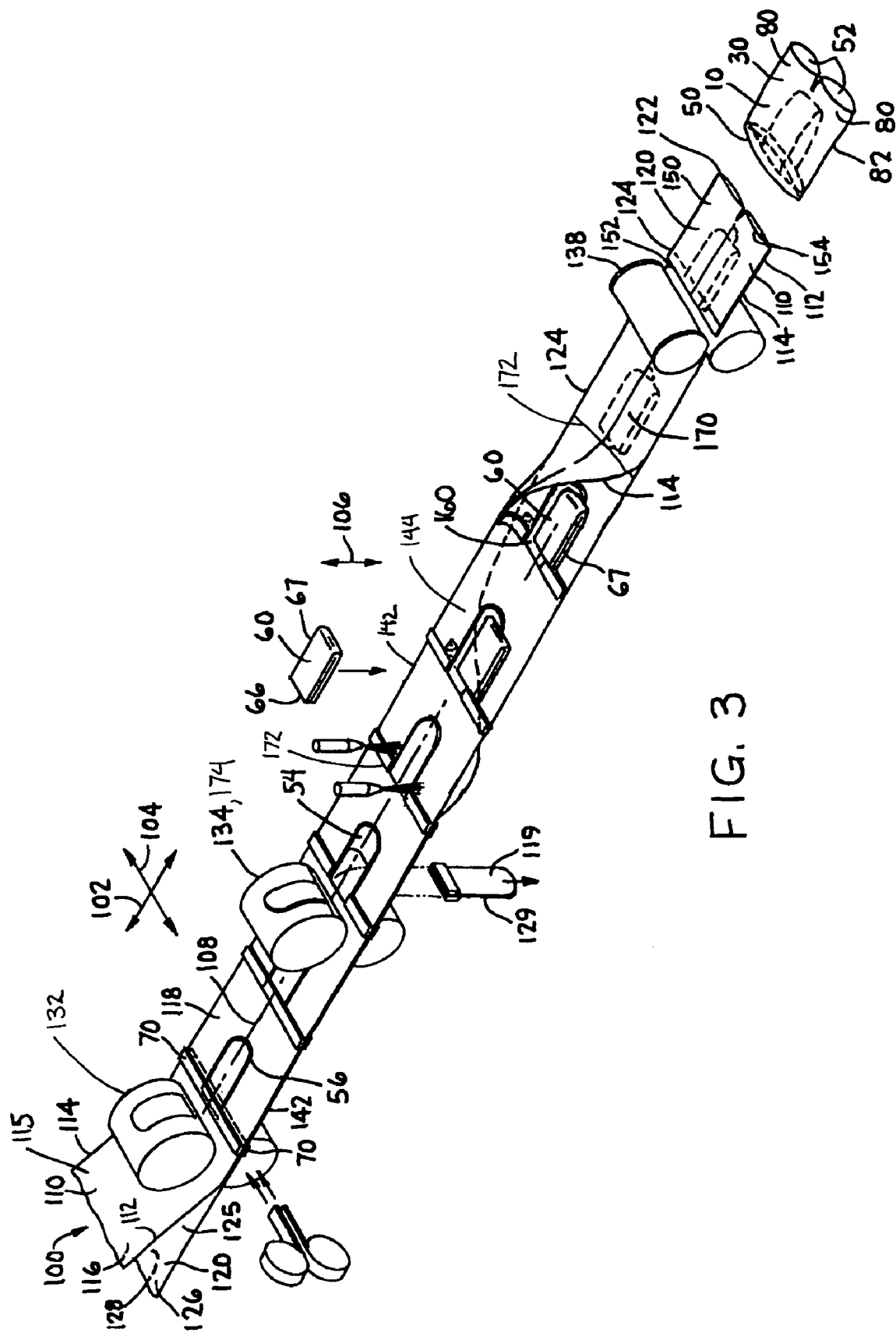
FIG. 3 representatively illustrates a schematic view of yet another aspect of the process of the present invention similar to FIGS. 1 and 2.
Figure 4B:
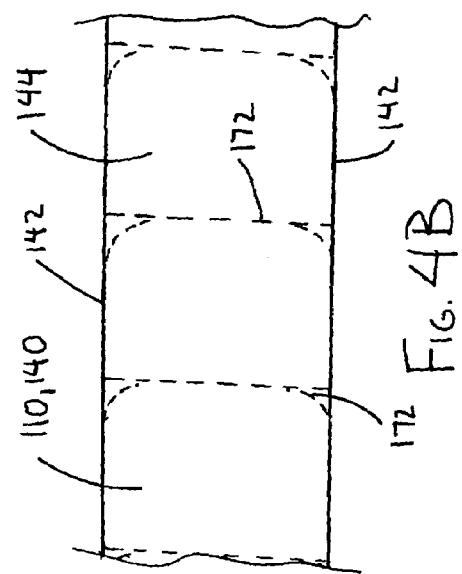
FIGS. 4A-4D representatively illustrate top views of different aspects of lines of weakness of the present invention with portions of the process and the garment omitted for clarity.
Figure 4D:
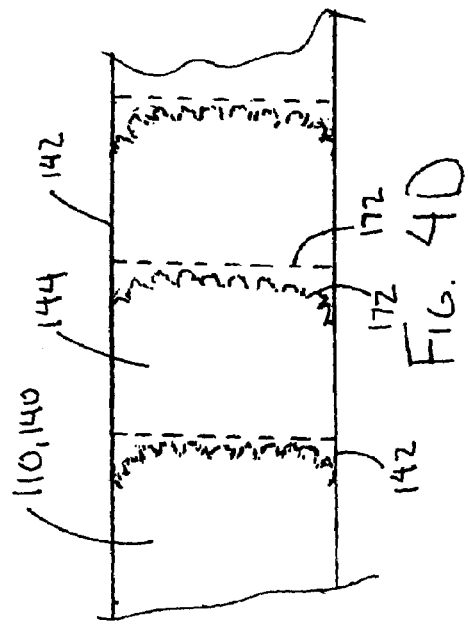
Figure 4A:
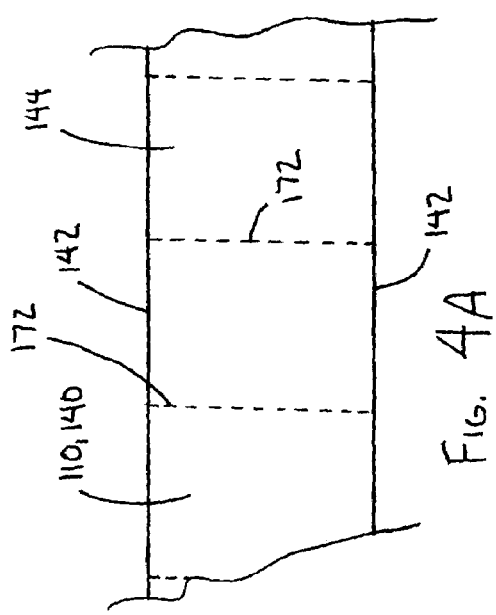
Figure 4C:
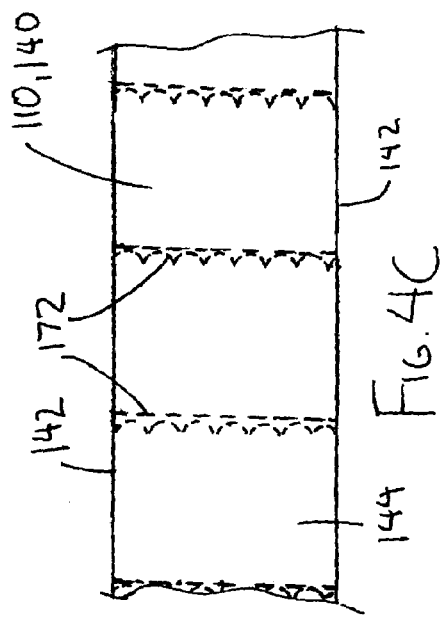

Referring now to the drawings, a process for separating discrete products from a product web is shown in its entirety at reference numeral 100 (FIGS. 1-3). In particular, the process 100 and the discrete products made thereby will be described in terms of making garments to be worn about the lower torso. Specifically, the process 100 will be described in terms of making boxer shorts, or shorts 10, but it should be readily recognized that the process of the present invention may be equally applicable with to other garments that may be worn about the lower torso such as pants, trunks, briefs, and other garments having a waist opening, a pair of leg openings, and optionally a pair of hanging legs. Further, it should be readily recognized that the process of the present invention may be equally applicable with the production of other products that may involve the separation of a product from a web of material following the manipulation of the web.

In addition, the shorts 10 of the present invention can include a garment shell and may further include an absorbent assembly 60, as will be described in greater detail below. Such garments and processes for making them, are described in U.S. Pat. No. 6,192,521 issued Feb. 27, 2001 to Alberts, et al., and U.S. patent application Ser. Nos. 10/837,343, and 10/954,508 filed in the name of Allen, et al., the disclosures of which are incorporated herein by reference to the extent that they are consistent (i.e., not in conflict) herewith.

The process 100 of the various aspects of the present invention defines a machine direction indicated at the arrow marked 102, and a cross machine direction indicated at the arrow marked 104 that is perpendicular to the machine direction 102. The process 100 also defines an orthogonal direction, indicated at the arrow marked 106 that is perpendicular to the plane created by the machine direction 102 and the cross machine direction 104. Further, the process also defines a process centerline 108 extending in the machine direction 102.

In the illustrated aspects, the process 100 is represented with the orthogonal direction 106 being generally vertical in orientation. Nonetheless, as can be readily appreciated by those of skill in the art, the orthogonal direction 106 of the present invention may also be generally horizontal in orientation or may otherwise be oriented and still be within the scope of the present invention.

The process includes transporting a product web 140 in the machine direction 102. The product web 140 can include any combination of materials that together provide a garment shell of the shorts 10. The product web 140 may be provided by a single web or a plurality of webs. For example, the product web 140 can include a first web 110 and optionally a second web 120. Thus, the first web 110 and the second web 120 may be provided and transported in the machine direction 102 to provide the product web 140. In addition, the product web 140 defines a pair of opposed product web side edges 142 that extend substantially in the machine direction 102 and a product web interior 144 disposed between the product web side edges 142.

In yet another alternative, it may be noted that the first web 110 and the second web 120 may be provided by separate webs or may alternatively be provided by a single web that is folded about the machine direction 102 and then subsequently separated (not shown). As representatively illustrated in FIGS. 1-3, the webs 110 and 120 can be provided in a substantially superposed relationship with each other.

The first web 110 of the product web 140 defines a first web first edge 112 and a first web second edge 114 that is opposite the first web first edge 112, and a first web interior 115 located within the first web first edge 112 and the first web second edge 114. The first web 110 also defines a first web inner surface 116 that is in facing relationship with the second web 120, and a first web outer surface 118 that is opposite the first web inner surface 116.

The second web 120 of the product web 140 defines a second web first edge 122 and a second web second edge 124 that is opposite the second web first edge 122, and a second web interior 125 that is located within the second web first edge 122 and the second web second edge 124. The second web 120 also defines a second web inner surface 126 that is in facing relationship with the first web 110, and a second web outer surface 128 that is opposite the second web inner surface 126.

Figure 6:
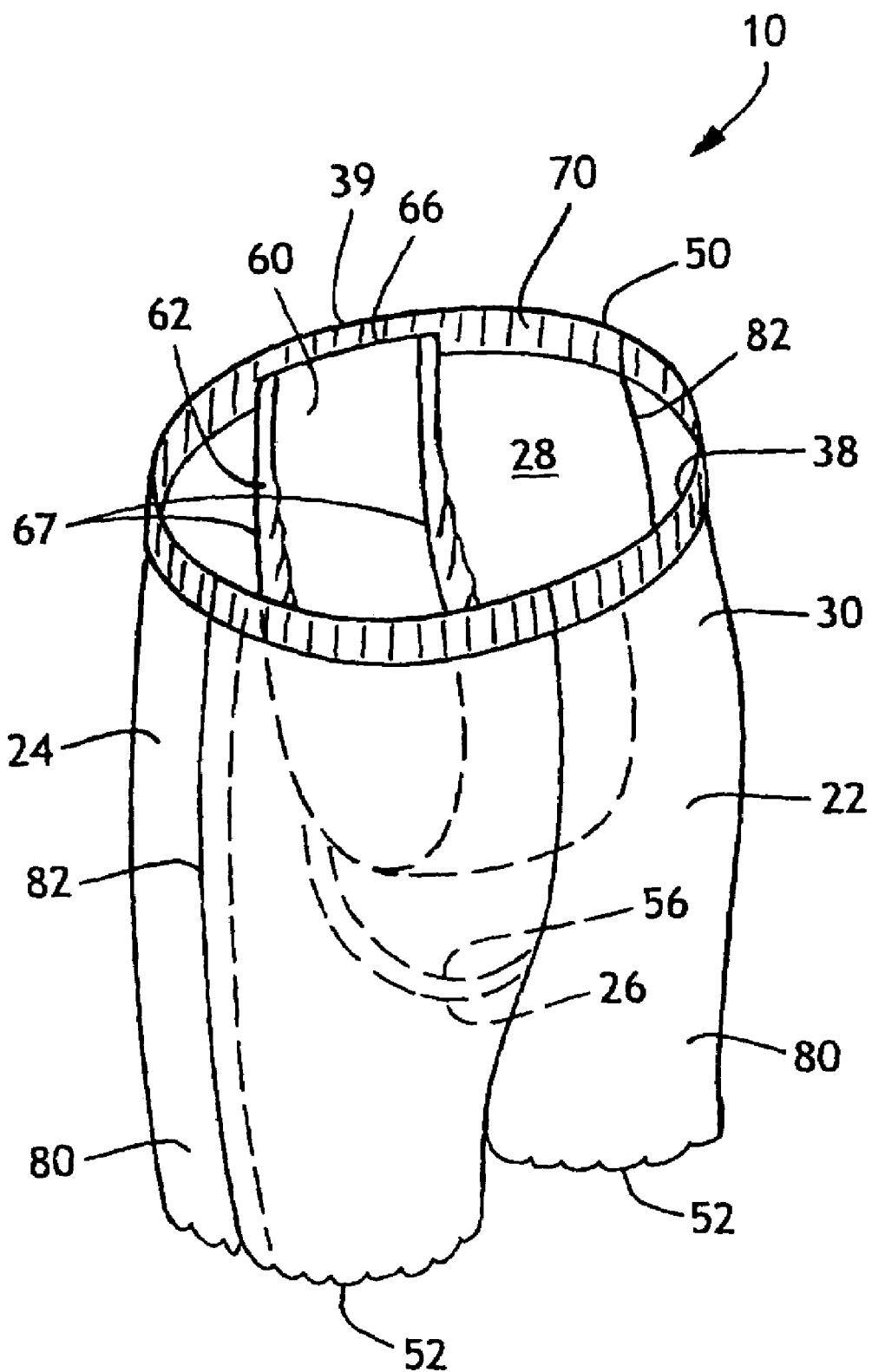
FIG. 6 representatively illustrates a perspective view of a completed garment made by one aspect of the process of the present invention.

As representatively illustrated in FIGS. 1-3, the webs 110 and 120 may be provided in at least a partially facing relationship, and may be in a substantially completely facing relationship. For example, the second web inner surface 126 may be in at least a partially facing relationship with the first web inner surface 116. It should be noted that the first and second web inner and outer surfaces 116, 118, 126, and 128 need not correspond to a body facing surface 28 and an exterior surface 30 of a resultant article when the article is produced (FIG. 6).

The process 100 is illustrated in FIGS. 1-3 as being configured to have the product web 140 pass through the process 100 in a generally horizontal orientation. Nonetheless, as can be readily appreciated by those of skill in the art, the process 100 may be configured to have the product web 140 pass through the process 100 in a generally vertical or other orientation and still be within the scope of the present invention. Suitably, the product web 140 can be initially provided to the process 100 in a generally planar position. For example, in configurations where the product web 140 is provided by a first web 110 and a second web 120, the webs 110 and 120 may initially be provided to the process 100 with the web edges 112, 114 and 122, 124 in a spaced relationship (FIGS. 1-3).

The product web 140 may be any suitable fabric to provide the shorts 10. In particular, the product web 140 may suitably be of materials which are comfortable against the skin and non-irritating. Since it is contemplated that the shorts 10 can be either disposable or durable (i.e., launderable), both nonwoven and woven materials are contemplated for the product web 140. For example, the product web 140 can be selected from a wide variety of materials, including elastic, stretchable, or nonstretchable materials. Any other type of nonwoven laminate or woven or knitted fabric known to those skilled in the art can also be used. The product web 140 can be a single layer of material or a multi-layered laminate structure. Moreover, as discussed above, the product web 140 may be provided by a plurality of webs (e.g., the webs 110 and 120).

Other suitable materials for the product web 140 include stretchable nonwovens, non-stretchable nonwovens, and nonwoven laminates including spandex and/or stretchable film. Spandex is any of various elastic textile fibers made chiefly of polyurethane. LYCRA® is a brand of spandex commercially available from Invista, Wichita, Kans., U.S.A. Alternatively, meltblown laminates are a suitable type of nonwoven laminate. Further, the material for the product web 140 may suitably, although not necessarily, have the ability to drape and conform to some extent to the body. In addition, the material can be, but need not be, opaque. Finally, the material used to provide the product web 140 can all be the same type of material or the product web 140 may be provided by a variety of materials. For example, in a configuration where the product web 140 is provided by a first web 110 and a second web 120, the first web 110 may or may not be the same as the material as the second web 120.

The product web 140 may be provided to and transported through the process 100 by various methods as are known in the art. For example, the product web 140 may be unwound and drawn through the process 100 via driven rolls, belt conveyors, chain conveyors, and the like or combinations thereof (not shown).

In configurations including a first web 110 and a second web 120, the first web 110 and the second web 120 may be attached to each other. For example, the first web 110 and the second web 120 may be provided to the process 100 attached at least intermittently to each other. Alternatively, the first web 110 and the second web 120 can be attached to each other in the process 100. In particular, the product web 140 may also include a crotch seam 56. The product web 140 may be provided to the process 100 with the crotch seam 56 already in place, or the crotch seam 56 may by incorporated in the product web 140 in the course of the process 100.

For example, as representatively illustrated in FIGS. 1-3, the product web 140 includes webs 110 and 120, which may be attached to one another to provide a crotch seam 56. In particular aspects, spaced portions of the product web 140 may be attached to one another at selected locations to provide a plurality of crotch seams 56. The seams 56 may be substantially continuous, or may be provided by a series of intermittent bonds. The crotch seam 56 may be of various shapes to produce the desired result. For example, the crotch seam 56 may be generally rectilinear, curvilinear (for example, circular or oval), generally "D" shaped, or generally "U" shaped. In particular aspects, the crotch seam 56 may be at least partially curvilinear to provide a garment with improved fit and comfort.

The crotch seam 56 may be imparted to the product web 140 by a bonding device 132 in various ways as are known in the art. For example, the crotch seam 56 may be formed by bonding portions of the product web 140 (e.g., bonding the first web 110 to the second web 120) as it travels in the machine direction 102. This bonding can be accomplished by using ultrasonic, pressure, or thermal bonding wheels rotating in a facing relationship to form the crotch seam 56. For example, an anvil wheel and a horn wheel defining a nip can be used to form the crotch seam 56. Alternatively, any suitable bonding method known in the art can be used, such as adhesives, sewing or the like.

The process 100 of the present invention may further include removing a portion of the product web 140 to define an opening in the product web 140, and particularly an opening in the product web interior 144. For example, the process 100 can include providing a crotch opening 54 in the product web 140, and suitably in the product web interior 144. In an alternative aspect, the product web 140 may be provided to the process 100 with an opening in the product web interior 144, such as the crotch opening 54 or a series of crotch openings 54 already in place. Suitably, the boundaries of the crotch opening 54 may be located completely within the product web side edges 142.

In a particular aspect, as representatively illustrated in FIGS. 1-3, the product web 140 is provided by webs 110 and 120. The process 100 may include selectively removing a portion of the first web 110 to define a first web removal portion 119. In addition, the process 100 of the present invention may include selectively removing a portion of the second web 120 to define a second web removal portion 129. As mentioned above, the portions of the webs 110 and 120 that are removed 119 and 129 can be located within the first web interior 115 and the second web interior 125. Suitably, when the product web 140 includes multiple layers of material, the portions that are removed 119 and 129 are generally aligned to define a crotch opening 54 that passes through the product web 140. For instance, as illustrated in FIGS. 1-3, the portions of the webs 110 and 120 that are removed 119 and 129 are generally in alignment with each other, and as such, define a common crotch opening 54 within the first web interior 115 and within the second web interior 125.

The crotch opening 54 may be any suitable shape to provide a crotch gap in the garment shell of the shorts 10. For example, the crotch opening 54 may be rectangular, oval shaped, curvilinear, rectilinear, and the like or combinations thereof. In particular, as representatively illustrated in FIGS. 1-3, the crotch opening 54 may be elongate in the machine direction 102 and may be at least partially curvilinear.

The providing of the crotch opening 54 may be accomplished by various methods as are known in the art. For example, a portion or portions of the product web 140 may be removed by a cutting device 134 such as cutting rolls, a die cutting assembly, a water cutting device or an ultrasonic cutter, or combinations thereof. Alternatively, other suitable cutting methods known in the art can be used. In yet another alternative, portions of the product web 140 may be perforated and may be removed subsequently in the process 100 to provide the crotch opening 54.

It should be noted that the step of providing the crotch seam 56 and the step of providing of the crotch opening 54 need not occur in a particular order, and moreover, need not happen sequentially. For example, the providing of a crotch opening 54 may occur prior to the formation of a crotch seam 56 or alternatively, as representatively illustrated in FIG. 3 the formation of the crotch seam 56 may occur prior to providing the crotch opening 54. In yet another alternative, the formation of the crotch seam 56 may occur at the same time as the formation of the crotch opening 54 (FIGS. 1 and 2). For instance, this may be accomplished by utilizing an ultrasonic bonder that is also capable of cutting.

As can be readily appreciated, the crotch opening 54 and the crotch seam 56 may be located as necessary in the product web 140, and may suitably be positioned proximate one another in the product web 140, or be otherwise associated. For example, as representatively illustrated in FIGS. 1-3, the crotch seam 56 may be located adjacent the crotch opening 54. In addition, as representatively illustrated in FIGS. 1-3, the crotch seam 56 may partially or fully circumscribe the crotch opening 54.

In the various aspects of the present invention, the process 100 can optionally include disposing an absorbent assembly 60 on the product web 140. For example, as representatively illustrated in FIGS. 1-3, an absorbent assembly 60 may be disposed on the product web 140 proximate the crotch opening 54. In particular, where the product web 140 is provided by a first and second web 110 and 120, the absorbent assembly 60 may be disposed on at least one of the webs 110 and 120. For example, as representatively illustrated in FIGS. 1-3, the absorbent assembly 60 may suitably be disposed on the first web 110 proximate the crotch opening 54.

The absorbent assembly 60 may be disposed on the product web 140 at various points throughout the process 100 as can be appreciated by one of skill in the art. Suitably, the absorbent assembly 60 may be disposed on the product web 140 while the product web is in an open configuration. That is, the product web 140 may be in a completely planar position and still be in an open configuration. Further, as will be discussed in greater detail below, portions of the product web 140 may be directed in the machine direction 102 or the cross machine direction 104, and the product web 140 is still in the open configuration. Thus, provided that portions of the product web 140 have not been attached together to form a waist opening 50 and a pair of leg openings 52, the product web 140 is in an open configuration. In a particular aspect, and as representatively illustrated in FIGS. 1-3, the product web 140 can be provided by a first web and a second web 110 and 120. In such a configuration, the absorbent assembly 60 can be disposed on at least one of the webs 110 and 120 while the edges 112, 114 and 122, 124 of at least one of the webs 110 and 120 are in a spaced relationship, and therefore the product web 140 is in an open configuration.

The process 100 of the various aspects of the present invention may also include directing at least a portion of the product web 140 in the cross machine direction 104 to define a product web folded portion 146. For example, the product web folded portion 146 may be provided by an overlapping portion, such as a first web overlapping portion 170 and/or a second web overlapping portion 160.

Specifically, in one aspect and as representatively illustrated in FIGS. 1-3, the second web 120 may be directed in the cross machine direction 104 to define a product web folded portion 146. In particular, a portion of the second web 120 proximate to either the second web first edge 122 or the second web second edge 124 can be directed in the cross machine direction 104 toward the process centerline 108 and the opposing edge 122 or 124 such that the second web 120 at least partially overlaps the crotch opening 54 to define a second web overlapping portion 160 (FIGS. 1, 1B, 2 and 3) and provide a product web folded portion 146. For example, the second web overlapping portion 160 may overlap the entire crotch opening 54, or alternatively the second web overlapping portion 160 may overlap only part of the crotch opening 54. In yet another alternative, a portion of the second web 120 may be directed in the cross machine direction 104 such that the second web overlapping portion 160 overlaps substantially the entire crotch opening 54 and the second web first edge 122 is substantially adjacent the second web second edge 124.

Thus, to direct a portion of the second web 120 in the cross machine direction 104, the second web 120 may be folded upon itself starting from the second web first edge 122. As a result, that portion of the second web 120 may be folded upon itself proximate the crotch seam 56 toward the process centerline 108 and the second web second edge 124 and desirably at least partially overlaps the crotch opening 54. Alternatively, in another aspect, a portion of the second web 120 may be folded upon itself starting from the second web second edge 124. As a result, that portion of the second web 120 is folded upon itself proximate the crotch seam 56 toward the process centerline 108 and the second web first edge 122 and desirably at least partially overlaps the crotch opening 54.

To provide the second web overlapping portion 160, the second web 120 is suitably directed in the cross machine direction 104 and folded upon itself from the second web edge 122 or 124 that is closer to the intended location of the absorbent assembly 60 (whether it has yet been disposed on the webs 110 or 120 or not), relative to the other second web edge 122 or 124.

For example, as representatively illustrated in FIGS. 1-3, the second web first edge 122 is proximate the location of the absorbent assembly 60 (disposed on the first web 110). Accordingly, the second web first edge 122 is included in the portion of the second web 120 that is directed in the cross machine direction 104 toward the process centerline 108 and the second web second edge 124 to at least partially overlap the crotch opening 54.

The directing of the second web 120 in the cross machine direction 104 to define a product web folded portion 146 can occur either before or after the absorbent assembly 60 is disposed upon the webs 110 and 120. In arrangements where the directing of the second web 120 occurs after the absorbent assembly 60 is disposed on one of the webs 110 or 120, the second web overlapping portion 160 may also overlap at least a portion of the absorbent assembly 60. That is, as representatively illustrated in FIGS. 1, 1B, 2 and 3, the portion of the second web 120 directed in the cross machine direction 104 may overlap the crotch opening 54 and overlap the absorbent assembly 60 to define a folded portion and the second web overlapping portion 160.

Further, the process 100 of the various aspects of the present invention may also include directing at least a portion of the first web 110 in the cross machine direction 104 to define a product web folded portion 146. In particular, the first web 110 can be directed in the cross machine direction 104 such that the first web 110 at least partially overlaps the absorbent assembly 60 to define a first web overlapping portion 170. For example, the first web overlapping portion 170 may overlap the absorbent assembly 60 entirely, or alternatively, as representatively illustrated in FIGS. 1, 1C, 2 and 3, the first web overlapping portion 170 may overlap a portion of the absorbent assembly 60. In addition, subsequent to the directing of the first web 110 in the cross machine direction 104, substantially the entire absorbent assembly 60 may be overlapped by the first web overlapping portion 170 and a portion of the second web 120 (FIGS. 1, 1C, 2 and 3).

In particular aspects, portions of the first web 110 proximate to either the first web first edge 112 or the first web second edge 114 may be directed in the cross machine direction 104 toward the process centerline 108 and the opposing edge 112 or 114. Thus, the first web 110 may be folded upon itself from the first web first edge 112 or the first web second edge 114. As a result, in one aspect, the portion of the first web 110 that is proximate the first web first edge 112 can be directed in the cross machine direction 104 toward the process centerline 108 and the first web second edge 114, and at least partially overlap the absorbent assembly 60. Further, the portion of the first web 110 that is proximate the first web first edge 112 can be directed in the cross machine direction 104 such that the first web first edge 112 is substantially adjacent to the first web second edge 114.

Alternatively, in another aspect, the portion of the first web 110 that is proximate the first web second edge 114 can be directed in the cross machine direction 104 toward the process centerline 108 and the first web first edge 112, and at least partially overlap the absorbent assembly 60. Further, the portion of the first web 110 that is proximate the first web second edge 114 can be directed in the cross machine direction 104 such that the first web second edge 114 is substantially adjacent to the first web first edge 112.

In particular aspects, in order to define a product web folded portion 146 and provide the first web overlapping portion 170, the first web 110 may suitably be directed in the cross machine direction 104 and folded upon itself from the first web edge 112 or 114 that is distant from the absorbent assembly 60 relative to the opposing edge 112 or 114. For example, as representatively illustrated in FIGS. 1-3, the first web second edge 114 is distant from the location of the absorbent assembly 60 (disposed on the first web 110) relative to the first web first edge 112 and is included in the portion of the second web 120 that is directed in the cross machine direction 104 to overlap the absorbent assembly 60. Moreover, the first web second edge 114 is placed substantially adjacent said first web first edge 112. In addition, the opening side edges 57 may become substantially aligned in said orthogonal direction 106 as a result.

The directing of the first web 110 and the second web 120 need not happen in any particular order. For example, the directing of the first web 110 may occur before the directing of the second web 120, or vice versa. Moreover, the directing of the webs may, but need not occur consecutively; for example, intervening steps may occur between the directing of the webs 110 and 120. Nonetheless, in configurations where the steps of directing of the first web 110 and the second web 120 have occurred in the process 100, the edges 112, 114, 122, and 124 of the webs 110 and 120 can become substantially aligned as a result.

For example, as representatively illustrated in FIGS. 1-3, upon the directing of the first web 110 and the second web 120 in the cross machine direction 104 as described above, the first web first edge 112 and the first web second edge 114 can be arranged to be substantially adjacent each other. Similarly, following the directing of the first web 110 and the second web 120 in the cross machine direction 104 as described above, the second web first edge 122 and the second web second edge 124 may be arranged to be substantially adjacent each other.

The directing of the product web 140 may be accomplished by various methods as are known in the art. For example, the directing may be achieved by a folding device such as folding boards, blade folding systems, air bars, and the like, or combinations thereof. Alternatively, other suitable directing methods known in the art can be used.

The process 100 of the present invention may also include the step of attaching a portion of the absorbent assembly 60 to the product web 140. For example, in one aspect, the absorbent assembly 60 may be attached to one or both of the webs 110 and 120 in a variety of configurations. As a result, when the shorts 10 are completed, the absorbent assembly 60 may be attached to the shorts 10 in the front region 22, in the back region 24, or in both regions 22 and 24. Further, the absorbent assembly 60 may be optionally attached to the shorts 10 in the crotch region 26 exclusively or while being attached in one or both of the front and back regions 22 and 24.

The absorbent assembly 60 may be attached to the product web 140 by a variety of methods as are known in the art. For example, the absorbent assembly 60 may be attached by adhesives, ultrasonic bonding, pressure bonding, sewing, and the like or combinations thereof. Moreover, as representatively illustrated in FIGS. 1 and 2, the absorbents may have attachment material applied on either side of the absorbent assembly 60 in order to accommodate the various configurations of the absorbent assembly 60 on the product web 140.

The absorbent assembly 60 may also be releasably attached to the product web 140, or even refastenably attached to the product web 140. Such a configuration may be advantageous where the shorts 10 are arranged to be durable or semi-durable, but yet still includes a disposable absorbent assembly 60. For example, the absorbent assembly 60 may be releasably attached to the product web 140 by using hook and loop fasteners or a cohesive material.

It should be noted that depending on the attachment method, the attachment material (i.e., an adhesive, a mechanical fastener, and the like) may be applied to the absorbent assembly 60, the product web 140, or both the absorbent assembly 60 and the product web 140 in order to achieve suitable attachment of the absorbent assembly 60.

The process 100 of the various aspects of the present invention further includes creating a line of weakness 172, for example with a line of weakness device 174, in the product web 140 and separating the product web 140 into a plurality of discrete individual elements such as products 150 (FIGS. 1-3) at the line of weakness 172. As will be discussed in greater detail below, the line of weakness 172 can extend substantially in the cross machine direction 104. As used herein, the phrase "line of weakness" can include perforations, a score line, a series of cuts, a crimp, or any other modification to the product web that will generally reduce its strength and urge a separation at that location upon application of a force substantially perpendicular to the line of weakness.

The products 150 can include at least the product web 140 and may optionally include other components (such as the absorbent assembly 60) depending upon where in the process 100 the separation occurs. In addition, separating the product web 140 into individual products 150 may also define product waist edges 152 in the product web 140. Similarly, separating the product web 140 may define product leg edges 154 opposite the product waist edges 152. In general, the product waist edges 152 and the product leg edges 154 may extend in the cross machine direction 104.

The creating of the line of weakness 172 may occur at various points in the process 100. For example, the creation of the line of weakness can occur before or after the crotch opening 54 is provided in the product web 140 and before or after disposing the absorbent assembly 60 on the product web 140. Suitably, however, the line of weakness 172 can be created while the product web 140 is in a substantially planar configuration and before portions of the product web 140 are directed in the cross machine direction 104. In such a configuration, the line of weakness 172 can help provide a pleasing waist edge 152 and/or leg edge 154 upon separation of the product 150 from the product web 140, even after the product web 140 has been manipulated by the process 100.

The line of weakness 172 can extend from proximate one product web side edge 142 to the other product web side edge 142 in substantially the cross machine direction 104. Alternatively, the line of weakness 172 may be suitably located in select portions of the product web to ensure that the product web maintains suitable strength to be manipulated by the process 100 and be separated only when desired by the process 100. Moreover, the line of weakness 172 can be continuous or discontinuous. In aspects where the product web 140 includes first and second webs 110 and 120, the line of weakness 140 can suitably be in place in each web 110 and 120.

In addition, the line of weakness 172 can be substantially linear or can alternatively be curvilinear. In a particular aspect, the line of weakness 172 can be curvilinear to provide a decorative appearance to the shorts 10 (FIGS. 2, 4B, 4C, 4D, 5 and 6). For example, as representatively illustrated in FIGS. 4C, 4D, 5 and 6, the line of weakness can be a series of scallop shapes.

In addition, the separation of the product web 140 into individual products 150 may occur at various points in the process 100. For example, the separation can occur before or after the crotch opening 54 is provided in the product web 140, before or after disposing the absorbent assembly 60 on the product web 140, and before or after portions of the product web 140 are directed in the cross machine direction 104. As can be readily appreciated by one of ordinary skill in the art, the separation of the product web 140 into individual products 150 will generally occur after the creation of the line of weakness 172. Optionally, the separation of the product web can occur immediately after the creation of the line or weakness 172, or can suitably occur downstream from the creation of the line of weakness 172.

In a particular aspect, the line of weakness 172 can be proximate the opening 54 (FIGS. 1-3). As such, the line of weakness 172 can suitably contribute to the creation of the waist opening 50 of the shorts 10 and as such the waist opening 50 will have a smooth, pleasing appearance that is aligned as desired with the crotch of the shorts 10. In this configuration, the opening 54 can be created substantially simultaneously with the line of weakness 172 (FIG. 3).

The creation of the line of weakness 172 can be conducted in various ways as are known in the art. For example, the line of weakness 172 can be provided by a die cutter, a perforation knife and anvil, an ultrasonic bonder, a pressure bonder, and the like, or combinations thereof.

Likewise, a separation device 138 can be used to separate the product web in a number of ways as are known in the art. For example, the portion of the product web 140 that is to be separated into a discrete product 150 may be nipped and accelerated away from the remaining product web to detach the product portion of the product web 140 away from the remaining product web 140.

The process 100 can further include creating multiple adjacent lines of weakness 172 and/or making multiple adjacent separations. For example, as representatively illustrated in FIGS. 2, 4B, 4C and 4D, the product web 140 can include multiple adjacent lines of weakness 172 to provide decorative leg edges 154 and/or waist edges 152. In particular, one line of weakness 172 may be curvilinear to provide a decorative edge and the adjacent line of weakness 172 may be substantially linear to provide a substantially straight edge 152 or 154 (FIGS. 2, 4B, 4C and 4D). As described above, these lines of weakness 172 can be subsequently separated at a desired point in the process 100. For example, a single separation device 138 can be used to break the product web 140 at the lines of weakness 172, or a plurality of separate separation devices 138 may be used to separate one line of weakness 172 and then the adjacent line of weakness 172.

In yet another alternative, the multiple separations can be created by a combination of a single line of weakness 172 and a pair of separations, one at the line of weakness 172 and another adjacent the line of weakness 172. For example, in one aspect, a substantially linear line of weakness 172 may be created and then subsequently separated as described above. Following this, a cutting device 134 may be used to sever the web adjacent the line of weakness 172 to create a substantially curvilinear edge 152 or 154.

Aspects of the present invention including multiple adjacent lines of weakness 172 and/or multiple adjacent separations can be suitable where it is desired to have one of the edges (i.e., the product waist edge 152 and the product leg edge 154) be curvilinear and the other edge (of the product waist edge 152 and the product leg edge 154) be substantially linear. Alternatively, aspects including multiple adjacent lines of weakness 172 and/or multiple adjacent separations can be suitable where adjacent edges 152 and 154 in the process 100 are both desired to be curvilinear but not in complementary patterns.

Portions of the product web 140 may be arranged and attached together to form a waist opening and a pair of leg openings 52 and to provide the shorts 10. For example, portions of the webs 110 and 120 may be attached together as representatively illustrated in FIGS. 1, 2 and 3. In particular, the first web first edge 112 may be attached to the first web second edge 114. Similarly, the second web first edge 122 may be attached to the second web second edge 124. Accordingly, shorts 10 with a waist opening 50, a pair of leg openings 52, and optionally a pair of hanging legs 80 may be provided (FIG. 6) by the process 100.

In a particular aspect, the attaching of the first web first edge 112 to the first web second edge 114 and the second web first edge 122 to the second web second edge 124 can form a pair of side seams 82. The side seams 82 can take any number of forms, including both refastenable and non-refastenable seams as is known in the art. The provision of the side seams 82 can be accomplished in the manner described in U.S. Pat. No. 5,046,272, issued Sep. 10, 1991 to Vogt et al., or in the manner described in U.S. Pat. No. 6,585,840, issued Jul. 1, 2003 to Alberts et al., or in the manner described in PCT Publications WO 01/87562 by Tomsovic, et al., WO 01/87217 by Durrance, et al., WO 01/87753 by Csida et al., and/or WO 01/87218 by Vogt, et al., all of which are incorporated herein by reference to the extent they are consistent (i.e., not in conflict) herewith. In particular and as representatively illustrated in FIGS. 1-3, the web edges 112, 114, 122 and 124 may be brought together by the directing of the webs 110 and 120 in the cross machine direction 104, as discussed above.

As is known in the art, the side seams 82 can be inward or outward butt seams (not shown) a welded bead seam (not shown), or lap seams (FIG. 6) or can be other seam types as are known in the art. It is contemplated that the side seams 82 may be fastened along only a portion of the distance between the waist opening 50 and the leg openings 52. For instance, the seams 82 may be fastened at the waist opening 50, leaving a slit open above the leg openings 52, such as in the style of some running or athletic garments. Alternatively, the side seams 82 may be fastened from the waist opening 50 to the respective leg openings 52.

Optionally, the process 100 may be configured to provide the shorts 10 such that the webs 110 and 120 may be attached together at a different time and/or location in order to form a pair of side seams 82 and a waist opening 50 and a pair of leg openings 52. That is, the process 100 may be configured to provide an intermediate garment element where the attaching of the first web first edge 112 to the first web second edge 114 and the attaching of the second web first edge 122 to the second web second edge 124 are completed at another location or by the end user. In particular, the edges 112, 114, 122, and 124 may include complementary fasteners, such as hook and loop fasteners, so that the webs 110 and 120 may be attached together at a later time. In such an arrangement, the shorts 10 may, for example, be packaged with the edges 112, 114, 122, and 124 unattached so that the end user may attach the webs 110 and 120 and obtain a customized fit.

The process 100 may further include attaching waist elastic material 70 to the product web 140. Suitably, the waist elastic material may be attached to the product web 140 while the product web is in an open configuration, or more suitably, in a planar configuration. For example, a portion of waist elastic material 70 may be attached to the first web 110 and a separate portion of waist elastic material 70 may be attached to the second web 120. The waist elastic material 70 may be attached to the webs 110 and 120 in a variety of locations. In a particular aspect and as representatively illustrated in FIG. 3, a portion of waist elastic material 70 may extend substantially in the cross machine direction 104 from the first web first edge 112 to the first web second edge 114. Similarly, another portion of waist elastic material 70 may extend substantially in the cross machine direction 104 from the second web first edge 122 to the second web second edge 124. Suitably, the waist elastic material 70 may be attached to the outer surfaces 118 and 128 of the webs 110 and 120, and still more suitably, the waist elastic material 70 may be generally aligned in the orthogonal direction 106 upon attachment to the webs 110 and 120 (FIG. 3). In such an arrangement, upon completion of the shorts 10, the waist elastic material 70 will be located on the garment bodyfacing surface 28. Alternatively, the portions of elastic material 70 may be attached to the first and second web inner surfaces 116 and 126, and as such, upon completion of the shorts 10, will be located on the garment exterior surface 30.

The waist elastic material 70 may be placed on the webs 110 and 120 as necessary to be located proximate the waist opening 50 of the finished shorts 10. Moreover, the attaching of the waist elastic 70 may occur at a variety of points during the process 100. For example, the waist elastic 70 may overlap the opening 54 and be subsequently cut out of the opening and removed, or as representatively illustrated in FIG. 3, be placed upon the webs 110 and 120 and then be subsequently removed when the opening 54 is formed. Desirably, the waist elastic material 70 is positioned upon the webs 110 and 120 so as to be proximate the waist edges 152 upon separation of the webs 110 and 120 into individual products 150.

The waist elastic material 70 can be formed of any suitable elastic material. As is well known to those skilled in the art, suitable elastic materials include sheets, strands or ribbons of natural rubber, synthetic rubber, or thermoplastic elastomeric polymers. In one particular embodiment, for example, the waist elastic 70 includes a plurality of dry-spun coalesced multifilament spandex elastomeric threads sold under the trade name LYCRA® and available from E.I. du Pont de Nemours and Company, Wilmington, Del., U.S.A. Alternatively, the elastic material includes a stretch-thermal laminate (STL), a neck-bonded laminated (NBL), a reversibly necked laminate, or a stretch-bonded laminate (SBL) material. Methods of making such STL, NBL and SBL materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; PCT Publication WO 01/88245 published on Nov. 22, 2001 in the name of Welch, et al.; all of which are incorporated herein by reference to the extent that they are consistent (i.e., not in conflict) herewith.

As mentioned above, the process 100 can include attaching an absorbent assembly 60 to at least a portion of the product web 140. The absorbent assembly 60 can be any structure which is generally compressible, conformable, non-irritating to the skin, and capable of absorbing and retaining liquids and certain body wastes. The absorbent assembly 60 can be manufactured in a wide variety of sizes and shapes, from a wide variety of liquid absorbent materials commonly used in the art, and may be stretchable, non-stretchable, or elastic. For example, the absorbent assembly 60 can suitably include a matrix of hydrophilic fibers, such as a Web of cellulosic fluff, mixed with particles of a high-absorbency material commonly known as superabsorbent material. In a particular embodiment, the absorbent assembly 60 includes a matrix of cellulosic fluff, such as wood pulp fluff, and superabsorbent hydrogel-forming particles. Suitable superabsorbent materials are available from various commercial vendors, such as Dow Chemical Company located in Midland, Mich. U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 60 includes a blend of wood pulp fluff and superabsorbent material. One suitable type of pulp is identified with the trade designation CR1654, available from U.S. Alliance, Childersburg, Ala. U.S.A., and is a bleached, highly absorbent sulfate wood pulp containing primarily soft wood fibers and about 16 percent hardwood fibers.

The absorbent assembly 60 can also incorporate other materials that are designed primarily to receive, temporarily store, and/or transport liquid along the mutually facing surface with absorbent assembly 60, thereby maximizing the absorbent capacity of the absorbent assembly. One suitable material is referred to as a surge layer (not shown) and includes a material having a basis weight of about 50 to about 120 grams per square meter (gsm), and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C. U.S.A.

The absorbent assembly 60 may also include a liner material that is intended to face the wearer in use. A suitable liquid permeable liner is a nonwoven bicomponent web having a basis weight of about 27 gsm. The nonwoven bicomponent can be a spunbond bicomponent web, or a bonded carded bicomponent web. Suitable bicomponent fibers include a polyethylene/polypropylene bicomponent fiber available from CHISSO Corporation, Osaka, Japan.

The absorbent assembly 60 may also include a suitable outercover intended to face away from the body of the wearer in use. The outercover desirably comprises a material that is substantially liquid impermeable. The outercover can be a single layer of liquid impermeable material, or may be a multi-layered laminate structure in which at least one of the layers is liquid impermeable. A suitable liquid impermeable film for use as liquid impermeable inner layer, or a single layer liquid impermeable outercover, is a 0.025 millimeter (0.75 mil) polyethylene film commercially available from Edison Plastics Company of South Plainfield, N.J. The liquid impermeable material can also be configured to permit vapors to escape from the interior of the absorbent body, while still preventing liquids from passing through the outercover. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

In particular embodiments, the absorbent assembly 60 is thin to provide a slim, comfortable, non-bulky short 10. Any suitable thin absorbent assembly may be used, such as for example, the thin absorbent described in WO 02/49565, published Jun. 27, 2002, by Sawyer et al., the disclosure of which is incorporated herein by reference to the extent it is consistent (i.e., not in conflict) herewith.

The absorbent assembly 60 optionally may include a pair of containment flaps 62 (FIGS. 5 and 6) which are configured to provide a barrier to the transverse flow of body exudates. Suitable constructions and arrangements for the containment flaps 62 are generally well known to those skilled in the art and are described in U.S. Pat. No. 4,704,116 issued Nov. 3, 1987 to Enloe, Which is incorporated herein by reference to the extent that it is consistent (i.e., not in conflict) herewith.

Figure 5:
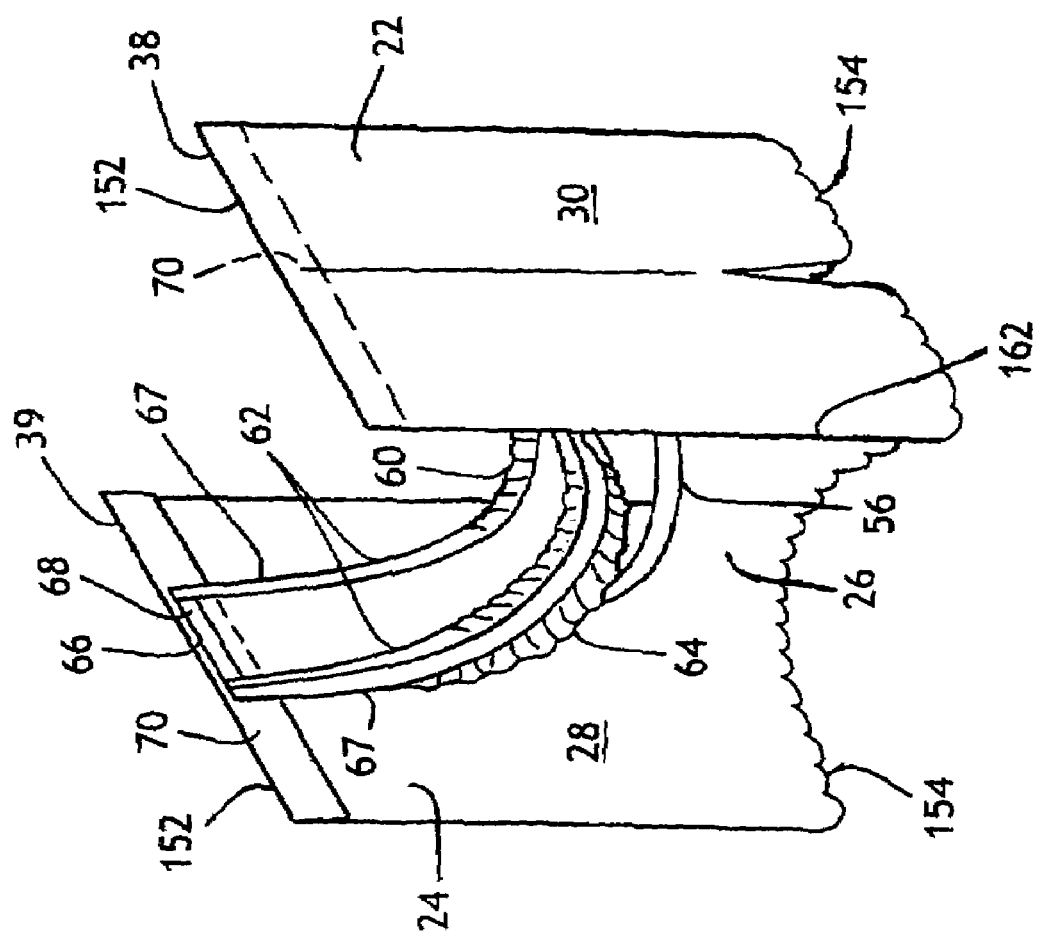
FIG. 5 representatively illustrates a perspective view of a partially completed garment made by one aspect of the process of the present invention.

To further enhance containment and/or absorption of body exudates, the absorbent assembly 60 may also suitably include absorbent assembly waist elastics 68 and leg elastics 64, as are known to those skilled in the art (FIGS. 5 and 6). The absorbent assembly waist elastics 68 can be operatively joined to the outercover and/or the liner along the opposing absorbent assembly end edges 66. The leg elastics 64 can be operatively joined to the outercover and/or the liner along the opposite absorbent assembly side edges 67.

The absorbent assembly waist elastics 68 and the absorbent assembly leg elastics 64 can be formed of any suitable elastic material. As is well known to those skilled in the art, suitable elastic materials include sheets, strands or ribbons of natural rubber, synthetic rubber, or thermoplastic elastomeric polymers. In one particular aspect, for example, the leg elastics 64 can include a plurality of dry-spun coalesced multifilament spandex elastomeric threads sold under the trade name LYCRA® and available from Invista, Wichita, Kans., U.S.A.

In the alternative, a pant-like garment insert could be used for the absorbent assembly 60. For example, the pant-like garment insert suitably includes a body side liner, an outer cover, an absorbent assembly between the body side liner and the outer cover, and side panels. Example of suitable inserts include a training pant, such as HUGGIES® PULL-UPS® Disposable Training Pants, and disposable underpants, such as GOODNIGHTS® Disposable Underpants, both manufactured by Kimberly-Clark Corporation, Neenah, Wis., U.S.A. Other alternative inserts include a cod-piece style insert as described in U.S. patent application Ser. No. 10/750,381 filed Dec. 30, 2003, in the name of Fitton.

In yet another alternative, a pad-type absorbent could be used for the absorbent assembly. The pad-type absorbent can be attached in the crotch-region 26 of the short 10. An example of a suitable pad-type absorbent is a feminine care pad such as KOTEX® Feminine Napkins, KOTEX® LIGHT-DAYS® Pantiliners, or an incontinence absorbent pad such as POISE® Feminine Guards and Pads or DEPEND® Guards for Men, all manufactured by Kimberly-Clark Corporation, Neenah, Wis., U.S.A.

As representatively illustrated in FIG. 6, an embodiment of a short 10 produced by the process 100 of the present invention can include a front region 22, a back region 24, a crotch region 26, a bodyfacing surface 28 which is configured to contact the wearer, and an exterior surface 30 opposite the bodyfacing surface 28 which is configured to face away from the surface of the wearer's body. The short 10 also defines a pair of opposed waist edges, which are designated front waist edge 38 and back waist edge 39. The front region 22 is contiguous with the front waist edge 38, and the back region 24 is contiguous with the back waist edge 39. The front region 22 includes the portion of the short 10 which, when worn, is positioned on the front of the wearer while the back region 24 includes the portion of the short 10 which, when worn, is positioned on the back of the wearer. The crotch region 26 of the short 10 includes the portion of the short which, when worn, is positioned between the legs of the wearer and covers the lower torso of the wearer.

As illustrated in FIG. 6, the front and back regions 22 and 24 are joined together at side seams 82 and the left and right sides of the short 10 are joined together at the crotch seam 56 to define a three-dimensional short configuration having a waist opening 50 and a pair of hanging legs 80 with leg openings 52. In particular aspects, the crotch seam 56 may follow a path which begins substantially at the front waist edge 38, extends through the crotch region 26, and terminates substantially at the back waist edge 39. In alterative embodiments, the crotch seam 56 can follow a path which begins below the front waist edge 38 on the front region 22 and terminates below the back waist edge 39 on the back region 24. As is known in the art, the crotch seam 56 can be an inward butt seam or a lap seam (not shown). In the alternative, the crotch seam 56 can be an outward butt seam.

In particular embodiments and as mentioned above, the short 10 can include an absorbent assembly 60. The absorbent assembly 60 can be attached to the short 10 at the front waist edge 38 and/or back waist edge 39, or at some point below the front waist edge 38 and/or the back waist edge 39 in the front region 22 and back region 24. Alternatively or additionally, the absorbent assembly 60 can be attached to the pant 10 in the crotch region 26.

The process 100 of the present invention is suitable for producing a series of garments (i.e., shorts 10), by transporting a product web 140 in a machine direction 102 and conducting at least a portion of the process steps described above and as illustrated in the figures. As can be readily appreciated, the distance between consecutive crotch openings 54 and crotch seams 56 in the process 100 may be varied to supply the desired length of leg covering provided by the hanging legs 80. Thus, if longer hanging legs 80 are desired, more distance can be placed between consecutive crotch openings 54 and bonds 56, and vice versa for shorter hanging legs 80.

Accordingly, the present invention provides a process 100 that is capable of providing a garment to be worn about the lower torso. In particular, the present invention provides a continuous process 100 that readily provides a garment including pleasing, even edges and can optionally include an absorbent assembly 60, and is capable of being run at elevated process speeds. Thus, the process 100 of the present invention is capable of mass producing aesthetically pleasing garments having hanging legs, crotch-depth and an absorbent assembly.

As various changes could be made in the above constructions and methods, without departing from the scope of the invention, it is intended that all matter contained in the above description and shown in the accompanying drawings shall be interpreted as illustrative and not in a limiting sense.

When introducing elements of the invention or the preferred aspect(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A process for separating a product web into discrete products, said process defining a machine direction and a cross machine direction; said product web defining a product web first side edge and a product web second side edge opposite said product web first side edge, a product web first surface and a product web second surface opposite said product web first surface, and a product web interior within said product web first side edge and said product web second side edge; said process comprising:

Transporting said product web in said machine direction, said product web comprising a first web and an opening in said product web interior;

Disposing an absorbent assembly proximate said opening;

Creating a line of weakness in said product web, said line of weakness extending substantially in said cross machine direction; and Separating said product web into discrete products at said line of weakness.

2. The process of claim 1 further comprising removing a portion of said product web to provide said opening in said product web interior.

3. The process of claim 1 wherein said line of weakness is proximate said opening.

4. The process of claim 1 further comprising directing a portion of said product web in said cross machine direction to define a product web folded portion.

5. The process of claim 4 further comprising disposing an absorbent assembly proximate said opening and attaching said absorbent assembly to said product web folded portion.

6. The process of claim 4 wherein said product web folded portion is provided by directing said first web in said cross machine direction.

7. The process of claim 1 wherein said product web further comprises a second web attached to said first web.

8. The process of claim 7 further comprising directing a portion of said second web in said cross machine direction to define a product web folded portion.

9. The process of claim 1 wherein said line of weakness extends from said product web first side edge to said product web second side edge.

10. The process of claim 1 wherein said line of weakness is a perforation.

11. The process of claim 1 wherein said line of weakness is discontinuous.

12. The process of claim 1 wherein said line of weakness is curvilinear.

13. The process of claim 1 wherein said line of weakness is a series of scallops.

14. The process of claim 1 wherein said step of creating said line of weakness occurs substantially simultaneously as said step of removing said portion of said product web.

15. The process of claim 1 wherein said discrete product element comprises a waist opening and a pair of leg openings.

16. A process for separating a product web into discrete products, said process defining a machine direction and a cross machine direction; said product web defining a product web first side edge and a product web second side edge opposite said product web first side edge, a product web first surface and a product web second surface opposite said product web first surface, and a product web interior within said product web first side edge and said product web second side edge; said process comprising:

Transporting said product web in said machine direction, said product web comprising a first web and an opening in said product web interior;

Disposing an absorbent assembly proximate said opening;

Creating a line of weakness in said product web, said line of weakness extending substantially in said cross machine direction;

Directing a portion of said product web in said cross machine direction to define a product web folded portion; and Separating said product web into discrete elements at said line of weakness.

17. The process of claim 16 further comprising removing a portion of said product web to provide said opening in said product web interior.

18. The process of claim 17 wherein said step of creating said line of weakness occurs before said step of removing said portion of said product web.

19. The process of claim 16 wherein said opening is proximate said line of weakness.

20. The process of claim 16 wherein said step of creating said line of weakness occurs before said step of directing said portion of said product web in said cross machine direction.

21. A process for separating a product web into discrete products, said process defining a machine direction and a cross machine direction; said product web defining a product web first side edge and a product web second side edge opposite said product web first side edge, a product web first surface and a product web second surface opposite said product web first surface, and a product web interior within said product web first side edge and said product web second side edge; said process comprising:

Transporting said product web in said machine direction, said product web comprising a first web, a second web attached to said first web and an opening in said product web interior;

Disposing an absorbent assembly proximate said opening;

Creating a line of weakness in said product web, said line of weakness extending substantially in said cross machine direction;

Directing a portion of said product web in said cross machine direction to define a product web folded portion; and Separating said product web into discrete products at said line of weakness.

* * * * *